United States Patent
Chang et al.

(10) Patent No.: US 10,683,521 B2
(45) Date of Patent: Jun. 16, 2020

(54) EXPRESSION CONSTRUCT FOR SENSING CELL DENSITY AND SUBSTRATE AVAILABILITY AND ITS USE IN CONVERSION OF HYDROXYCINNAMIC ACIDS

(71) Applicant: Nanyang Technological University, Singapore (SG)

(72) Inventors: Matthew Wook Chang, Singapore (SG); Tat Ming Samuel Lo, Singapore (SG); Chueh Loo Poh, Singapore (SG)

(73) Assignee: Nanyang Technological University, Singapore (SG)

( * ) Notice: Subject to any disclaimer, the term of this patent is extended or adjusted under 35 U.S.C. 154(b) by 0 days.

(21) Appl. No.: 14/409,227

(22) PCT Filed: Jun. 12, 2013

(86) PCT No.: PCT/SG2013/000242
§ 371 (c)(1),
(2) Date: Dec. 18, 2014

(87) PCT Pub. No.: WO2013/191651
PCT Pub. Date: Dec. 27, 2013

(65) Prior Publication Data
US 2015/0176039 A1    Jun. 25, 2015

Related U.S. Application Data

(60) Provisional application No. 61/661,593, filed on Jun. 19, 2012.

(51) Int. Cl.
| | |
|---|---|
| *C12N 15/74* | (2006.01) |
| *C12P 7/62* | (2006.01) |
| *C12N 9/00* | (2006.01) |
| *C12N 15/67* | (2006.01) |
| *C12N 9/88* | (2006.01) |
| *A61K 38/00* | (2006.01) |

(52) U.S. Cl.
CPC ............... *C12P 7/62* (2013.01); *C12N 9/88* (2013.01); *C12N 9/93* (2013.01); *C12N 15/67* (2013.01); *C12Y 402/01* (2013.01); *C12Y 602/01012* (2013.01)

(58) Field of Classification Search
CPC .... C12P 7/62; C12N 9/88; C12N 9/93; C12N 15/67; C12Y 602/01012; C12Y 402/01
See application file for complete search history.

(56) References Cited

U.S. PATENT DOCUMENTS

| | | | |
|---|---|---|---|
| 2003/0159184 A1* | 8/2003 | Fabijanski | C12N 15/743 |
| | | | 800/294 |
| 2012/0322101 A1* | 12/2012 | Bobrowicz | C07K 16/32 |
| | | | 435/68.1 |
| 2014/0011871 A1* | 1/2014 | Rockhill | A61K 47/44 |
| | | | 514/481 |
| 2015/0167092 A1* | 6/2015 | Kartalov | C12Q 1/6883 |
| | | | 506/4 |
| 2015/0197760 A1* | 7/2015 | Los | C12N 9/2408 |
| | | | 435/471 |
| 2016/0319311 A1* | 11/2016 | Eppelmann | C12N 9/1029 |

OTHER PUBLICATIONS

Ezezika et al. CatM regulation of the benABCDE operon: functional divergence of two LysR-type paralogs in Acinetobacter baylyi ADP1., Appl Environ Microbiol. (2006), vol. 72(3), pp. 1749-1758.*
Collier et al., Regulation of Benzoate Degradation in Acinetobacter sp. Strain ADP1 by BenM, a LysR-Type Transcriptional Activator., Bacteriol. (1998), vol. 180(9), pp. 2493-2501.*
Romero-Arroyo et al. catM encodes a LysR-type transcriptional activator regulating catechol degradation in Acinetobacter calcoaceticus., J Bacteriol. (1995), vol. 177(20), pp. 5891-5898.*
Peng et al. (2014) Activation of gab cluster transcription in *Bacillus thuringiensis* by γ-aminobutyric acid or succinic semialdehyde is mediated by the Sigma 54-dependent transcriptional activator GabR, BMC Microbiol., vol. 14:306, pp. 1-12.*
Fuhrer et al. (2007) Computational Prediction and Experimental Verification of the Gene Encoding the NAD+/NADP+-Dependent Succinate Semialdehyde, J. Bacteriol., vol. 189, pp. 8073-8078.*
Metzner et al. (2004) Multiple stress signal integration in the regulation of the complex σS-dependent csiD-ygaF-gabDTP operon in *Escherichia coli*, vol. Mol. Microbiol., vol. 51. No. 3, pp. 799-811.*
Kurihara et al. (2010) A Putrescine-Inducible Pathway Comprising PuuE-Ynel in Which gamma-Aminobutyrate Is Degraded into Succinate in *Escherichia coli* K-12, J. Bacteriol., vol. 189, pp. 8073-8078.*

(Continued)

*Primary Examiner* — Paul J Holland
*Assistant Examiner* — Samuel W Liu
(74) *Attorney, Agent, or Firm* — Seed IP Law Group LLP

(57) ABSTRACT

An Expression system; isolated nucleic acid molecule or host cell comprising: (i) A first gene encoding for a first enzyme linked to a first promoter, wherein the first promoter is a time delay promoter; (ii) A second gene encoding for a second enzyme capable of using the product generated by the first enzyme as a substrate, wherein the second gene is operably linked to a second promoter, wherein the second promoter is inducible by the product generated by the first enzyme; (iii) Optionally, a third gene encoding a transcription factor that represses expression of the second gene in the absence of the product generated by the first enzyme, wherein the third gene is operably linked to a third promoter that regulates expression of the third gene; and its use in producing a product such as hydroxybenzaldehyde.

25 Claims, 6 Drawing Sheets
Specification includes a Sequence Listing.

(56) References Cited

OTHER PUBLICATIONS

Maciag et al. (2011) In vitro transcription profiling of the pS subunit of bacterial RNA polymerase: re-definition of the pS regulon and identification of pS-specific promoter sequence elementsNucleic acid Res., vol. 39, pp. 5338-5355.*
Peng et al. (2014) Activation of gab cluster transcription in Bacillus thuringiensis by γ-aminobutyric acid or succinic semialdehyde is mediated by the Sigma 54-dependent transcriptional activator GabR, BMC Microbiol., vol. 14, pp. 1471-2180.*
Prokaryotes (2018) Evolution and Diversity: Prokaryotes, pp. 1-2.*
BioMineWiki (2018, updated) Prokaryote versus eukaryote, http://wiki.biomine.skelleftea.se/wiki/index.php/Prokaryote, pp. 1-3.*
Amann et al. (2016) After All, Only Millions?, MBio, vol. 7, issue 4, pp. 1-2.*
Uzzau et al. (2002) Differential accumulation of Salmonella [Cu,Zn] superoxide dismutases SodCI and SodCII in intracellular bacteria: correlation with their relative contribution to pathogenicity, Mol. Microbiol., vol. 46, No. 1, pp. 147-156.*
Shimada et al. (2004) Classification and Strength Measurement of Stationary-Phase Promoters by Use of a Newly Developed Promoter Cloning Vector, J. Bacteriol., vol. 186, pp. 7112-7122.*
Battistoni et al. (2000) Increased Expression of Periplasmic Cu,Zn Superoxide Dismutase Enhances Survival of *Escherichia coli* Invasive Strains within Nonphagocytic Cells, Infect. Immun., vol. 68, pp. 30-37.*
Extended European Search Report, dated Feb. 5, 2016, for corresponding European Application No. 13807048.7—1402 / 2877582, 9 pages.
Gitzinger et al., "The food additive vanillic acid controls transgene expression in mammalian cells and mice," *Nucleic Acids Research* 40(5):e37, 2011. (15 pages).
Golby et al., "Identification and Characterization of a Two-Component Sensor-Kinase and Response-Regulator System (DcuS-DcuR) Controlling Gene Expression in Response to $C_4$-Dicarboxylates in *Escherichia coli*," *Journal of Bacteriology* 181(4):1238-1248, 1999.
Maithreye et al., "Delay-Induced Transient Increase and Heterogeneity in Gene Expression in Negatively Auto-Regulated Gene Circuits," *PLoS One* 3(8):e2972, 2008. (10 pages).
Zhang et al., "Design of a dynamic sensor-regulator system for production of chemicals and fuels derived from fatty acids," *Nature Biotechnology* 30(4):354-359. (7 pages).
Achterholt et al., "Identification of *Amycolatopsis* sp. Strain HR167 genes, involved in the bioconversion of ferulic acid to vanillin," *Appl Microbiol Biotechnol* 54:799-807, 2000.
Barghini et al., "Vanillin production using metabolically engineered *Escherichia coli* under non-growing conditions," *Microbial Cell Factories* 6:13, 11 pages, 2007.
Bartolome et al., "An *Aspergillus niger* Esterase (Ferulic Acid Esterase III) and a Recombinant *Pseudomonas fluorescens* subsp. *cellulosa* Esterase (XylD) Release a 5-5' Ferulic Dehydrodimer (Diferulic Acid) from Barley and Wheat Cell Walls," *Applied and Environmental Microbiology* 63(1):208-212, Jan. 1997.
Bhathena et al., "Microencapsulated bacterial cells can be used to produce the enzyme feruloyl esterase: preparation and in-vitro analysis," *Applied Microbiology Biotechnology* 75:1023-1029, 2007.
Buanafina, "Feruloylation in Grasses: Current and Future Perspectives," *Molecular Plant* 2(5):861-872, Sep. 2009.
Calisti et al., "Regulation of ferulic catabolic genes in *Pseudomonas fluorescens* BF13: involvement of a MarR family regulator," *Applied Microbiology Biotechnology* 80:475-483, 2008.
Di Gioia et al., "Metabolic engineering of *Pseudomonas fluorescens* for the production of vanillin from ferulic acid," *Journal of Biotechnology* 156:309-316, Aug. 2011.
Dodd et al., "Biochemical Analysis of a β-D-Xylosidase and a Bifunctional Xylanase-Ferulic Acid Esterase from a Xylanolytic Gene Cluster in *Prevotella ruminicola* 23," *Journal of Bacteriology* 191(10):3328-3338, May 2009.
Gasson et al., "Metabolism of Ferulic Acid to Vanillin—A Bacterial Gene of the Enoyl-SCoA Hydratase/Isomerase Superfamily Encodes an Enzyme for the Hydration and Cleavage of a Hydroxycinnamic Acid SCoA Thioester," *The Journal of Biological Chemistry* 273(7):4163-4170, 1998.
Kasai et al., "Characterization of FerC, a MarR-type transcriptional regulator, involved in transcriptional regulation of the ferulate catabolic operon in Sphingobium sp. strain SYK-6," *FEMS Microbiol Lett* 332:68-75, 2012.
Lee et al., "Directing Vanillin Production From Ferulic Acid by Increased Acetyl-CoA Consumption in Recombinant *Escherichia coli*," *Biotechnology and Bioengineering* 102(1):200-208, Jan. 1, 2009.
Lee et al., "Heterologous protein production in *Escherichia coli* using the propionate-inducible pPro system by conventional and auto-induction methods," *Protein Expression and Purification* 61:197-203, 2008.
McClendon et al., "Novel bacterial ferulic acid esterase from *Cellvibrio japonicus* and its application in ferulic acid release and xylan hydrolysis," *Biotechnol. Lett.* 33:47-54, 2011.
Muheim et al., "Towards a high-yield bioconversion of ferulic acid to vanillin," *Appl Microbiol Biotechnol* 51:456-461, 1999.
Nocadello et al., "The new pLAI (*lux* regulon based auto-inducible) expression system for recombinant protein production in *Escherichia coli*," *Microbial Cell Factories* 11:3, 13 pages, 2012.
Overhage et al., "Biotransformation of eugenol to vanillin by a mutant of *Pseudomonas* sp. strain HR199 constructed by disruption of the vanillin dehydrogenase (*vdh*) gene," *Appl Microbiol Biotechnol* 52:820-828, 1999.
Peng et al., "Isolation and Characterization of Thermophilic Bacilli Degrading Cinnamic, 4-Coumaric, and Ferulic Acids," *Applied and Environmental Microbiology* 69(3):1417-1427, Mar. 2003.
Plaggenborg et al., "Functional analyses of genes involved in the metabolism of ferulic acid in Pseudomonas putida KT2440," *Appl Microbiol Biotechnol* 61:528-535, Mar. 2003.
Plaggenborg et al., "The coenzyme A-dependent, non-β-oxidation pathway and not direct deacetylation is the major route for ferulic acid degradation in *Delftia acidovorans*," *FEMS Microbiology Letters* 205:9-16, 2001.
Qi et al., "Isolation and characterization of a ferulic acid esterase (Fae1A) from the rumen fungus *Anaeromyces mucronatus*," *Journal of Applied Microbiology* 110:1341-1350, 2011.
Saeidi et al., "Engineering microbes to sense and eradicate *Pseudomonas aeruginosa*, a human pathogen," *Molecular Systems Biology* 7:521, 11 pages, 2011.
Tsao et al., "Autonomous induction of recombinant proteins by minimally rewiring native quorum sensing regulon of *E. coli*," *Metaboic Engineering* 12:291-297, 2010.
Wong et al., "Engineering *Saccharomyces cerevisiae* to produce feruloyl esterase for the release of ferulic acid from switchgrass," *J Ind Microbiol Biotechnol* 38:1961-1967, 2011.
Yamada et al., "Vanillin production using *Escherichia coli* cells over-expressing isoeugenol monooxygenase of *Pseudomonas putida*," *Biotechnol Lett* 30:665-670, 2008.
Yan et al., "Chemical compositions of four switchgrass populations," *Biomass and Bioenergy* 34:48-53, 2010.
Yoon et al., "Enhanced Vanillin Production from Recombinant *E. coli* Using NTG Mutagenesis and Adsorbent Resin," *Biotechnol. Prog.* 23:1143-1148, 2007.
Yoon et al., "Production of Vanillin from Ferulic Acid Using Recombinant Strains of *Escherichia coli*," *Biotechnology and Bioprocess Engineering* 10:378-384, 2005.
Zhang et al., "Design of a dynamic sensor-regulator system for production of chemicals and fuels derived from fatty acids," *Nature Biotechnology* 30(4):354-359, Apr. 2012.

* cited by examiner

EXPRESSION CONSTRUCT FOR SENSING CELL DENSITY AND SUBSTRATE AVAILABILITY AND ITS USE IN CONVERSION OF HYDROXYCINNAMIC ACIDS

STATEMENT REGARDING SEQUENCE LISTING

The Sequence Listing associated with this application is provided in text format in lieu of a paper copy, and is hereby incorporated by reference into the specification. The name of the text file containing the Sequence Listing is 690148.470USPC_SEQUENCE_LISTING.txt. The text file is 10 KB, was created on Dec. 15, 2014, and is being submitted electronically via EFS-Web.

CROSS-REFERENCE TO RELATED APPLICATION

This application claims the benefit of priority of U.S. Provisional Patent Application No. 61/661,593 filed Jun. 19, 2012, the contents of which being hereby incorporated by reference in its entirety for all purposes.

FIELD OF THE INVENTION

Prokaryotic recombinant systems designed to operate at a high cell density.

BACKGROUND OF THE INVENTION

Hydroxycinnamic acids are a class of polyphenols having a C6-C3 skeleton. These compounds are hydroxy derivative of cinnamic acid. Hydroxycinnamic acids are phenolic phytochemicals found in a wide range of plants and fungi and are found abundantly in nature. For example, hydroxycinnamic acid such as caffeic acid and ferulic acid (4-hydroxy-3-methoxy-trans-cinnamic acid) can constitute about 3% of the dry weight of graminaceous plants (1) such as flax seed with the highest concentrations found in seeds and the bran of graminaceous plants.

Ferulic acid links arabinoxylans to lignin, the lignin-ferulate-xylan complex (FIG. 3) can contribute to the recalcitrance of plant tissues, thereby lowering the efficiency of the biomass conversion in biofuel production (2). As such, to reduce substrate complexity and increasing cellulose accessibility, biomass can be pretreated with hemicellulases such as xylanase and feruloyl esterase (3-5), with ferulic acid released as a major by-product (6). With the espousal of using switchgrass (a rich source of ferulic acid) (7) as the renewable source for biofuel production, the by-product, ferulic acid is currently a waste product.

Another type of hydroxycinnamic acid found in graminaceous plants is p-coumaric acid (4-hydroxybenzaldehyde). Oxidizing 4-hydroxybenzaldehyde can lead to the production of p-hydroxybenzoate which is used as a monomer for synthesizing liquid crystal polymers. The aromatic compound p-hydroxybenzoate is a building block of liquid crystal polymers, high performance plastics that are employed in electronic devices such as mobile phones electronic devices for telecommunication and aerospace applications. p-hydroxybenzoate is also used in chemical and food packaging applications. The cascade bio-synthesis pathway of p-coumaric acid to p-hydroxybenzoate is realized through the biological pathway of 4-hydroxybenzaldehyde formation by feruloyl-CoA synthetase (Fcs), followed by oxidation to p-hydroxybenzoate by enoyl-CoA hydrotase (Ech).

Hydroxycinnamic acid can provide a substrate for the production of high value chemicals. Another such economic interest is the production of vanillin (4-hydroxy-3-methoxy-benzaldehyde), the key flavor component of vanilla from hydroxycinnamic acids such as ferulic acid. Vanillin is used extensively in food, cosmetic, and pharmaceutical industries (8). Due to popular demand, vanillin derived from natural sources such as vanilla pod (*Vanilla planifolia*) can reach as high as US$4000/kg (9). The bio-synthesis of vanillin from ferulic acid can be realized through the established biological pathway of feruloyl-CoA thioester formation by feruloyl-CoA synthetase (Fcs), followed by hydration to β-hydroxy derivative and then cleavage to give vanillin and acetyl-CoA by enoyl-CoA hydrotase (Ech) (10) (See FIG. 4). Many studies had reported the use of these enzymes from various microorganisms for the bio-production of vanillin (11-16). Microorganisms such as *Pseudomonas fluorescens* BF13 (11), *Pseudomonas* sp. HR199 (12), *Amycolatopsis* sp. HR167(13), *Pseudomonas putida* (14), *Bacillus subtilis* (15), *Delia acidovorans* (16), and *Streptomyces setonii* (17) had been proposed as candidates for the bioconversion of ferulic acid to vanillin. However, these organisms produce natural ferulic acid degraders that are capable of using vanillin as a source of carbon and energy. Thus, to avoid any reduction in the yield, downstream genes such as vanillin dehydrogenase (Vdh) which converts vanillin to vanillic acid may have to be knocked out (12).

An alternative approach has been developed to use a non-native vanillin producer such as *Escherichia coli* (14, 18-21) to host the genes responsible for converting ferulic acid to vanillin. Among bacteria, recombinant *E. coli* has been touted as the most efficient biocatalyst for vanillin production (11).

However, in many of the studies where *E. coli* was used as the host for bio-vanillin production, artificial induction with common inducers such as isopropyl-b-D-thiogalactoside (IPTG) and arabinose were performed. Although generally, artificial induction offers the control over protein expression, artificial induction in many cases is less favorable due to high economic cost of inducers, inducer toxicity, incompatibilities with industrial scale-up and detrimental growth conditions (22). Thus, these issues often limit the usage of the artificial inducible systems in industrial scale protein production. Using recombinant *E. coli* as a biocatalyst for vanillin production with and without the inhibiter IPTG Lee at al. (19) demonstrated that the addition of IPTG only further decreased production of vanillin.

A substitute to the artificial inducible systems is the use of constitutive promoters which can initiate protein expression in the absence of the inducers. Though constitutive promoters may offer comparative economic advantage, strong constitutive expression of recombinant proteins may divert the cellular resources away from essential metabolic activities to overproduction of unnecessary RNAs, and proteins. This may subsequently leads to growth retardation or adaptive responses from the host cells that may reduce yield and productivity (23). To overcome such problem, previous work by Barghini et al. (2007) (20) had tried to use low-copy number vector in vanillin synthesis. Nonetheless, the instability issue brought by strong constitutive promoter still remains.

One strategy for that has been seen in recent studies for avoiding instability is to use the *Vibrio fischeri*'s quorum sensing system for cell density regulated protein production (22), fatty acid bio-sensor for biodiesel production (23) and pathogen detection for anti-microbial peptide production (24). This strategy uses the lux regulon. It is unclear if the lux regulon would work in the complex control of hydroxycinnamic acid catabolism.

Gamma-aminobutyrate (GAB) expression is activated under carbon or nitrogen deficient cell stress. Expression of GAB is activated by the sigma factor RpoS a stress induced transcription factor often transcribed in the stationary phase of bacterial cell growth. There are about 70 stress genes having RpoS dependent expression.

SUMMARY

A first aspect of the invention includes an expression system comprising:
(i) A first gene encoding for a first enzyme linked to a first promoter, wherein the first promoter is a time delay promoter;
(ii) A second gene encoding for a second enzyme capable of using the product generated by the first enzyme as a substrate, wherein the second gene is operably linked to a second promoter, wherein the second promoter is inducible by the product generated by the first enzyme;
(iii) Optionally, a third gene encoding a transcription factor that represses expression of the second gene in the absence of the product generated by the first enzyme, wherein the third gene is operably linked to a third promoter that regulates expression of the third gene.

Another aspect of the invention includes an isolated nucleic acid molecule comprising (i) A first gene encoding for a first enzyme linked to a first promoter, wherein the first promoter is a time delay promoter; (ii) A second gene encoding for a second enzyme capable of using the product generated by the first enzyme as a substrate, wherein the second gene is operably linked to a second promoter, wherein the second promoter is inducible by the product generated by the first enzyme; (iii) Optionally, a third gene encoding a transcription factor that represses expression of the second gene in the absence of the product generated by the first enzyme, wherein the third gene is operably linked to a third promoter that regulates expression of the third gene.

Another aspect of the invention includes a host cell comprising the expression system or the isolated nucleic acid molecule of the invention.

Another aspect of the invention includes a method of converting a substrate to a product comprising the steps of: (a) subjecting the expression system or the host cell according the invention under conditions that allow the expression of the first and second enzyme; and (b) isolating the product from said host cell.

Other aspects of the invention would be apparent to a person skilled in the art with reference to the following drawings and description of various non-limiting embodiments.

BRIEF DESCRIPTION OF THE DRAWINGS

The drawings are not necessarily drawn to scale, emphasis instead generally being placed upon illustrating the principles of various embodiments. In the following description, various embodiments of the invention are described with reference to the following drawings.

DETAILED DESCRIPTION

Figure 1:
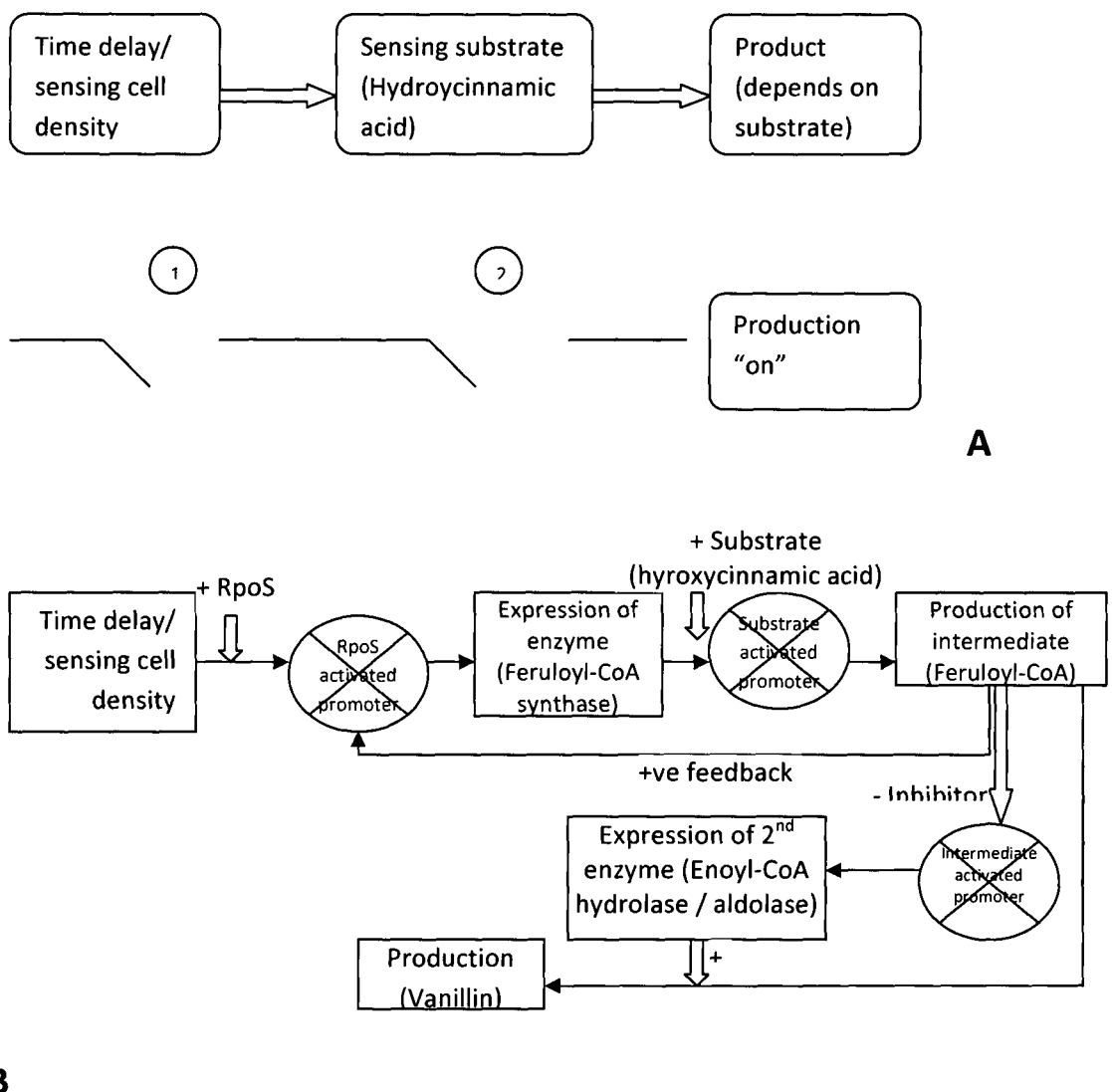
FIG. 1. A schematic of the construct having a Tandem switch design indicated as switch 1 (1) and switch 2 (1), that resembles a logic "AND" gate A; and a schematic Block diagram of our design indicating the positive feedback loop for Ferylic-CoA synthase (Fcs) expression is included B. This design reduces the response time for production.

We have constructed a recombinant expression system to improve biological system stability for economical bioproduction.

Accordingly a first aspect of the invention includes an expression system comprising: (i) A first gene encoding for a first enzyme linked to a first promoter, wherein the first promoter is a time delay promoter; (ii) A second gene encoding for a second enzyme capable of using the product generated by the first enzyme as a substrate, wherein the second gene is operably linked to a second promoter, wherein the second promoter is inducible by the product generated by the first enzyme; (iii) Optionally, a third gene encoding a transcription factor that represses expression of the second gene in the absence of the product generated by the first enzyme, wherein the third gene is operably linked to a third promoter that regulates expression of the third gene.

The expression system may be designed to operate in vitro. Preferably the expression system is a cell based expression system, more preferably a prokaryotic cell based system.

Preferably the time delay promotor is activatable by a transcription factor comprising amino acid sequence set forth in SEQ ID NO. 2. preferably, the transcription factor is RpoS sigma factor also known as E sigma 38. While this expression product is primarily known to activate stress related genes in the stationary phase of bacterial cell growth the inventors have been able to use the onset of transcription of the RpoS sigma factor after the exponential growth phase of a bacterial population as a time delay promoter to activate non-stress genes at a time that cell density is stable. In this way expression system is activatable by RpoS and can be switched on in a procaryotic cell when cell population density is optimal for production.

The sequence set forth in SEQ ID NO. 2 includes any functional varient of Rpos. This may vary from the sequence by 1, 2, or more amino acids. In the context of the present invention, a functional varient is taken to include an amino acid sequence which is at least 60, 70, 80 or 90% identical, preferably at least 95 or 98% identical at the amino acid level over at least 20, 50, 100, 200, 300 or 400 amino acids with the amino acid sequences set out in SEQ ID. NO 2. In particular, functional varient should typically be considered with respect to initiation or activation of expression of stress genes known to be activatable by RpoS or initiation or activation of expression of the first heterogonous nucleic acid of at least 2 fold. Preferably, expression increases 2-100 fold, or 10 to 50 fold.

Preferred polypeptides of the invention comprise a contiguous sequence having greater than 50, 60 or 70% homology, more preferably greater than 80 or 90% homology, to one or more of amino acids of SEQ ID NO: 2.

We espoused a new method for gene expression. It is an autonomous regulated system of induction with sensors and feedback loops. Not only does this system independent of costly artificial inducers, it is capable of regulating the protein expression level based on desired features such as substrate concentration and cell density. By introducing sensors and feedback loops, we are implementing the "control theory" which is widely used in the mature engineering fields (such as mechanical and electrical engineering) into the biological systems. The control theory provides the means for attaining optimal performance in dynamic biological system and achieving system stability through corrective action. By implementing control and self-monitoring in recombinant protein expression, it allows the biological systems to produce what is needed, thereby preventing the wastage of precious cellular resources and compromising key metabolic activities that may affect cell growth.

The control theory can be applied in our genetic circuit through introducing other bio-sensors. The second nucleic acid promoter sequence activatable by a substrate acts as a substrate sensor and the first nucleic acid promotor sequence acts as a time-delay sensor element. The substrate sensor allows regulation of protein expression. The system would only trigger the protein production when the substrate, is available. Further, in order for the cells to grow well, a time delay is needed before activating the system through the bio-sensor of the first nucleic acid promotor sequence. This is to ensure that in the presence of substrate inducers, cells growing from low cell density (e.g. single colony inoculation) would not experience overwhelming metabolic stress that may lead to growth retardation. The time-delay element would provide the cells some time to reach a higher cell density before activating the bio-sensor of the second nucleic acid promoter sequence, so that the amount of substrate inducers per cell would be lower and thus less detrimental to growth.

Our mode of gene induction in bio-catalysts is more economically attractive. Compared to existing methods which use costly inducers such as IPTG, our method for vanillin production eliminates the need for external inducers and can bring considerable material cost savings in the industrial conversion.

Preferably, the time delay promoter sequence comprises a consensus sequence set forth in SEQ ID NO: 1. This sequence $nCTAn_3Tn_6$ is conserved in the promotor region of operons where expression is dependent on the presence of RpoS. Usually the consensus sequence is located in the −10 region of the operon where the CTA is at −13 to −11 and T is at −7 variations may exist provided the first nucleic acid promoter sequence is activatable by RpoS in that the nucleic acid sequence adjacent the time delaypromoter has increased expression of at least 2 fold when RpoS is present. Preferably, expression increases 2-100 fold, or 10 to 50 fold.

There are many stress genes known to have RpoS dependent expression. Many of these genes have been shown to have a promotor region comprising the consensus sequence mentioned above. The promotor region of any such gene may be separated from its natural structural genes that express a stress peptide and placed 5' adjacent the first gene expressing the first enzyme being a heterogonous nucleic acid able to express the first enzyme thereby forming a time delay promotor. The promotor region of any stress genes known to have RpoS dependent expression can be used as the time delay promotor. Preferably, the time delaypromoter is selected from gabDT promoter; otsA promoter; katE promoter; osmY promoter; yhiUV promoter; ecnB promoter; dps promoter; osmE promopter; sodC promoter; rpsV promoter; yahoo promoter and tnaA promoter. In one embodiment the time delaypromoter comprises a gabDT promoter set out in SEQ ID NO: 3.

The second nucleic acid promoter sequence is activatable by the substrate interfering with an inhibitor of the second nucleic acid promoter sequence thereby allowing expression of the second gene, a heterogeneous nucleic acid. There are many procaryotic operons that consists of the repressor/inhibitor, promoter, operator and the structural genes.

Any such operon may be used in the isolated nucleic acid expression system described herein.

In a preferred embodiment the second gene is able to express a enoyl-CoA hydrolase. Preferably the gene encoding the enoyl-CoA hydrolase may comprise the sequence set forth in SEQ ID NO. 4 or a functional variant. In this embodiment the second promoter operably linked to the second gene comprises a sequence set forth in SEQ ID NO. 6 activatable by the product expressed by the first gene.

In a preferred embodiment the optional third gene encodes the transcription factor PP3359 that represses expression of the second gene enoyl-CoA hydrolase in the absence of the product Ferulic-Co-A generated by the first enzyme, wherein the third gene is operably linked to a third promoter that regulates expression of the third gene. Preferably the third gene comprise the sequence set forth in SEQ ID NO. 7 encoding the transcription factor comprise the sequence set forth in SEQ ID NO. 8 or a functional variant.

Another aspect of the invention includes an isolated nucleic acid molecule comprising (i) A first gene encoding for a first enzyme linked to a first promoter, wherein the first promoter is a time delay promoter; (ii) A second gene encoding for a second enzyme capable of using the product generated by the first enzyme as a substrate, wherein the second gene is operably linked to a second promoter, wherein the second promoter is inducible by the product generated by the first enzyme; (iii) Optionally, a third gene encoding a transcription factor that represses expression of the second gene in the absence of the product generated by the first enzyme, wherein the third gene is operably linked to a third promoter that regulates expression of the third gene.

The term "isolated nucleic acid" as used herein refers to any nucleic acid molecule in any possible configuration, such as single stranded, double stranded or a combination thereof. Isolated nucleic acids include for instance DNA molecules, RNA molecules, analogues of the DNA or RNA generated using nucleotide analogues or using nucleic acid chemistry, locked nucleic acid molecules (LNA), peptide nucleic acid molecules (PNA) and tecto-RNA molecules. DNA or RNA may be of genomic or synthetic origin and may be single or double stranded. Such nucleic acid can be e.g. mRNA, cRNA, synthetic RNA, genomic DNA, cDNA, synthetic DNA, a copolymer of DNA and RNA, oligonucleotides, etc.

In a preferred embodiment the first gene of the isolated nucleic acid molecule is a heterogeneous nucleic acid that is able to express the first enzyme comprising feruloyl-CoA synthase and the second gene is a heterogeneous nucleic acid that is able to express the second enzyme comprising enoyl-CoA hydrolase. The first gene able to express feruloyl-CoA synthase may comprise the sequence set forth in SEQ ID NO. 4. The second gene able to express enoyl-CoA hydrolase may comprise the sequence set forth in SEQ ID NO. 5. In a preferred embodiment the optional third gene encodes the transcription factor pp3359 that represses expression of the second gene enoyl-CoA hydrolase in the absence of the product Ferulic-Co-A generated by the first enzyme, wherein the third gene is operably linked to a third promoter that regulates expression of the third gene. Preferably the third gene comprise the sequence set forth in SEQ ID NO. 7 encoding the transcription factor comprise the sequence set forth in SEQ ID NO. 8 or a functional variant.

In this embodiment the preferred substrate may be a hydroxycinnamic acid or a derivative thereof. Preferably, the hydroxycinnamic acid or derivative thereof may include caffeic acid; ferulic acid; p-coumaric acid; and cinnamic acid. In one embodiment the hydroxycinnamic acid is ferulic acid. In another embodiment the hydroxycinnamic acid is p-coumaric acid. In various embodiments the nucleic acid expression system may convert ferulic acid or caffeic acid to vanillin. In various embodiments the nucleic acid expression system may convert p-coumaric acid, to 4-hydroxybenzaldehyde. Oxidizing 4-hydroxybenzaldehyde can lead to the production of p-hydroxybenzoate. Thus, our system is versatile in generating different products depending on the type of substrate present.

The isolated nucleic acid molecule may be comprised in a vector such as a plasmid as any vectors or expression systems known in the art.

Another aspect of the invention comprises a host cell comprising the expression system or the isolated nucleic acid molecule described herein. The host cell is a prokaryotic cell, preferably a bacterial cell. Preferably the host cell is a cell that does not naturally express polypeptides involved in the breakdown of the product. In one embodiment the host cell is an *E. coli* cell.

Another aspect of the invention includes a method of converting a substrate to a product comprising the steps of: (a) subjecting the expression system or the host cell according to the invention under conditions that allow the expression of the first and second enzyme; and (b) isolating the product from said host cell.

In one embodiment step a) may include cultivating the host cell under conditions that allow the expression of the first and second enzyme.

Preferably the product is a hydroxybenzaldehyde. In one embodiment the product is vanillin having formula 1

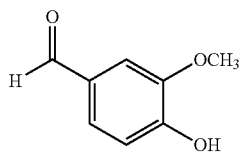 [SMILES: COc1cc(C=O)ccc1O]

In one embodiment the product is p-hydroxybenzoate having formula 2

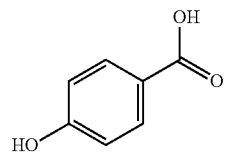

EXAMPLES

In the design of our production system, we have created a tandem switch for the activation of the hydroxycinnamic acid metabolism system. This tandem switch can be regarded as a logic AND gate device. Only when both hydroxycinnamic acid and threshold cell density are present, a product such as vanillin would be produced. This tandem switch is illustrated in FIG. 1A.

To construct the switches and the vanillin production device, the list of biological parts which were used is stated in Table 1. Using these parts, we have developed a ferulic acid sensor coupled with a time-delay element for the regulation of the vanillin genes, fcs and ech. To develop the ferulic acid sensor, we studied and implemented the ferulic acid sensing mechanism in *Pseudomonas. putida* KT2440 in *Escherichia. coli* BL21(DE3). However, for system stability and fast response time to ferulic acid, the design of the genetic circuit is important.

TABLE 1

List of biological parts used in the genetic circuit for vanillin production

| No. | Name | Type | Function |
|---|---|---|---|
| 1 | $P_{gabDT}$ | Promoter | Time-Delay |
| 2 | $P_{PP3359}$ | Promoter | Regulates PP3359 |
| 3 | $P_{ech}$ | Promoter | Essential component of ferulic acid sensor |
| 4 | PP3359 | Transcription Factor | Represses Pech. For ferulic acid sensing |
| 5 | fcs | Gene | Converts ferulic acid to feruloyl-CoA |
| 6 | ech | Gene | Converts feruloyl-CoA to vanillin |

To shorten the response time to the ferulic acid, we had modeled our genetic circuit layout after the ferulic catabolic operon in *P. putida* KT2440. fcs together with its time-delay promoter are placed downstream of ech gene. Hence, once activated, $P_{ech}$ would lead to the transcription of ech and fcs. Additional fcs transcripts together with the ones transcribed from the time-delay promoter may lead to higher Fcs expression. We expected higher Fcs concentration to shorten the response time of $P_{ech}$ activation and increase ferulic acid uptake. Increase ferulic acid uptake leads to higher formation of feruloyl-CoA, and this drives a faster activation of $P_{ech}$, which in turn transcribes ech and fcs genes. Thus, a positive feedback loop is created (FIG. 1B), and the system behaves as an amplifier for vanillin enzymes expression, especially for Fcs. FIG. 1B describes the signal flow in the block diagram of the vanillin production system. The chief signal in the system is the feruloyl-CoA. Not only does it increases fcs transcripts and activates Ech expression, it is involved in the next step to vanillin production. Once all the feruloyl-CoA has been converted to vanillin, $P_{ech}$ expected to be repressed by PP3359, and the amplifier behavior to be reduced to naught, leaving only the constitutive expression of Fcs.

Our engineered E. coli may convert ferulic acid or caffeic acid to vanillin or p-coumaric acid, to 4-hydroxybenzaldehyde. Oxidizing 4-hydroxybenzaldehyde can lead to the production of p-hydroxybenzoate. Thus, our engineered E. coli is versatile in generating different products depending on the type of substrate present.

Figure 2:
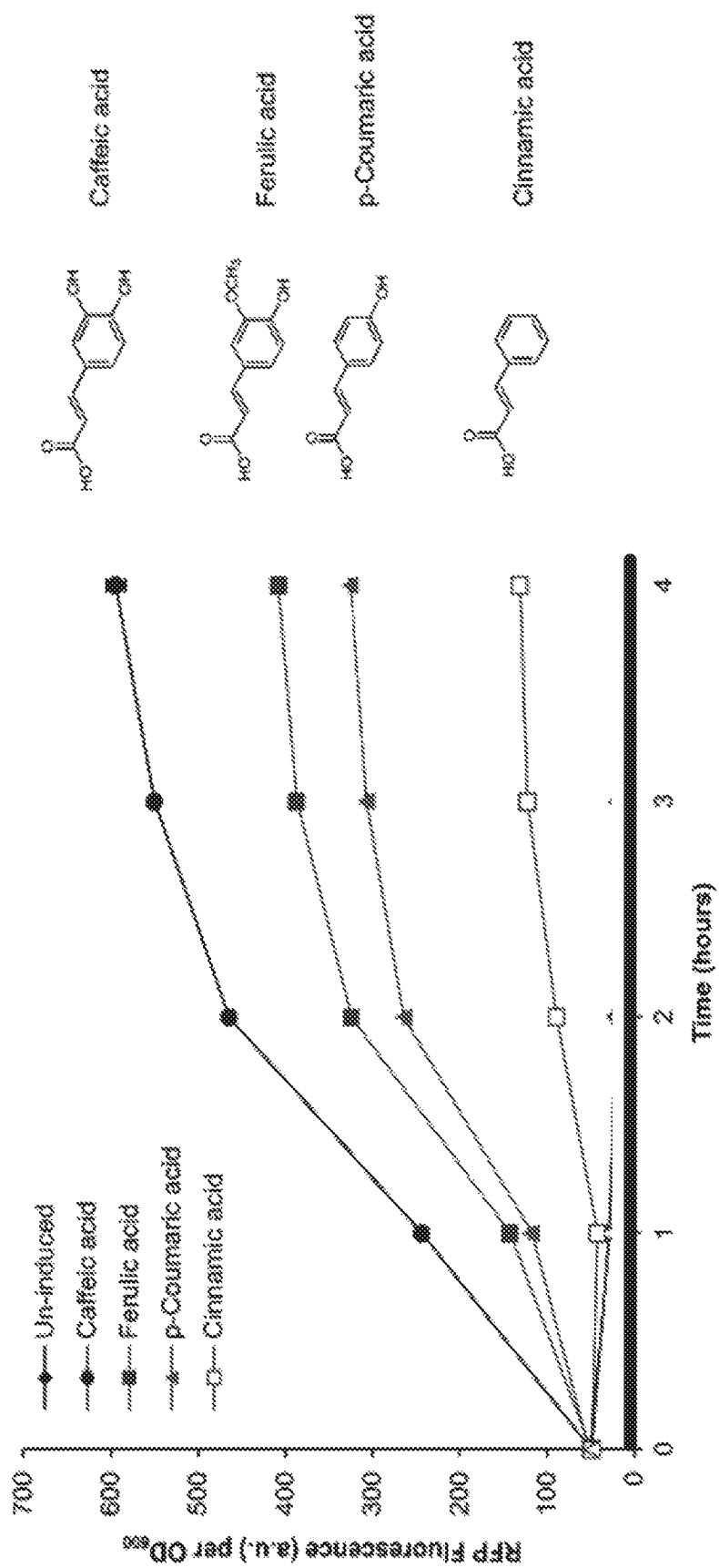
FIG. 2. Our designed genetic system responds to a wide variety of hydroxycinnamic acids, namely caffeic, ferulic and p-coumaric acids, which can be derived from lignin.
Figure 3:
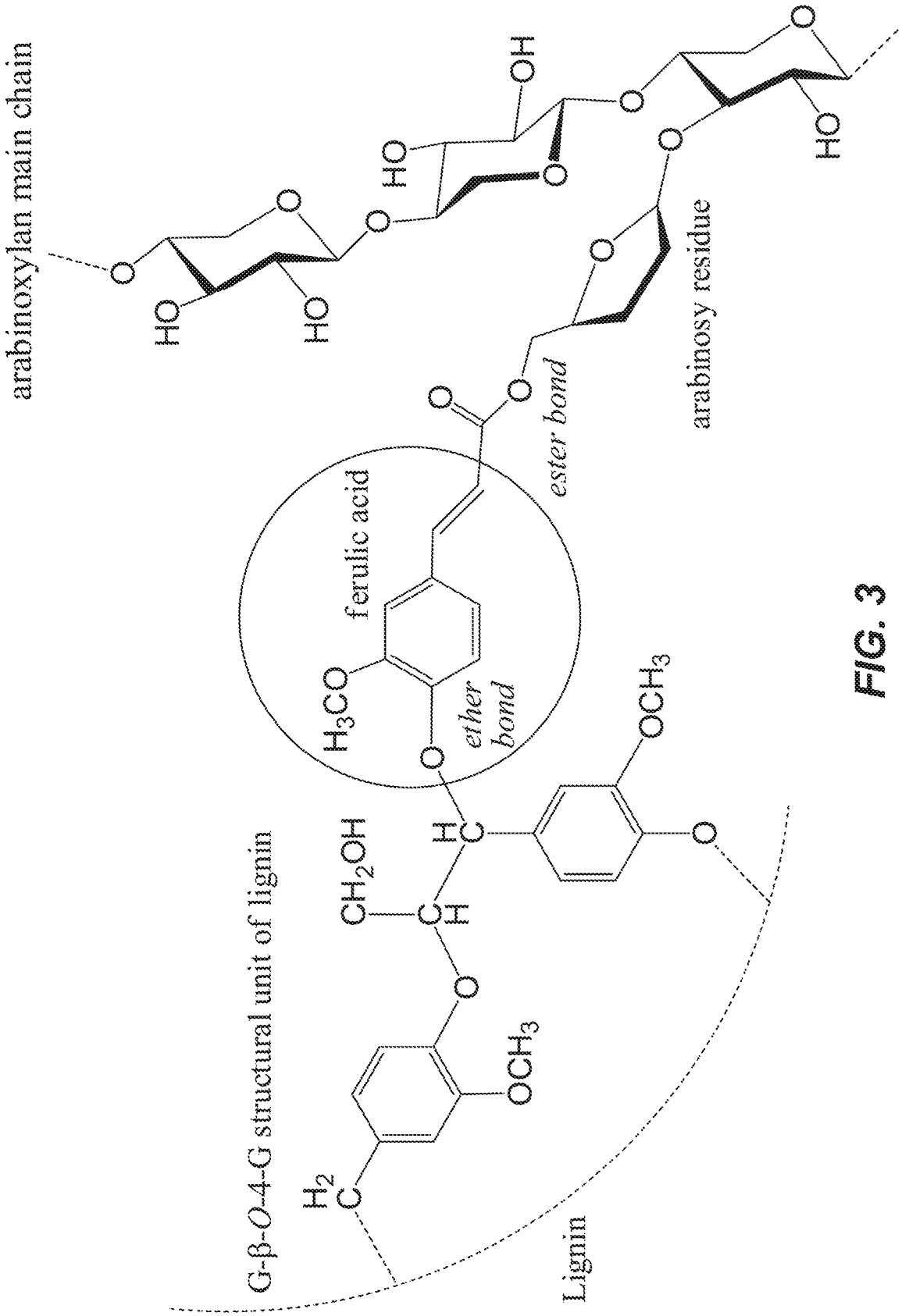
FIG. 3. A depiction of a lignin-ferulate-xylan complex often constitutes a high amount of ferulic acid in plants especially graminaceous plants such as Switch grass. During pre-treatment process, ferulic acid can be released as a by-product.
Figure 4:
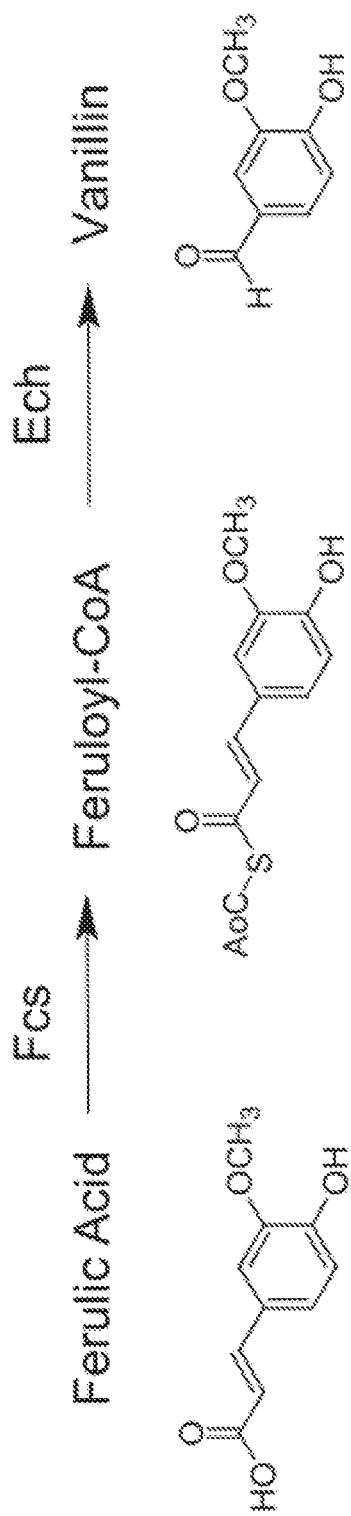
FIG. 4 Biological pathway for conversion of ferulic acid to vanillin.

Our engineered E. coli can sense a variety of lignin-derived hydroxycinnamic acids. Our designed genetic system not only allowed host cells to auto-regulate enzyme expression based on substrate availability, it also enabled host cells to respond to a wide range of lignin-derived hydroxycinnamic acids such as ferulic, p-coumaric and caffeic acid, making them highly useful and flexible for hydroxycinnamic acid conversion (FIG. 2).

Our system improves biological system stability for economical production of enzymes for vanillin conversion. We strongly believe that in the whole cell bioconversion of ferulic acid to vanillin, bacteria growth is closely related to the efficacy of the bio-catalysis. By having a large bio-catalytic population in the shortest time, it leads to a faster production of vanillin. Thus, here we demonstrated that by improving host cell viability, the time to reach saturation for the vanillin bioconversion would be reduced. To achieve robust cell growth in E. coli, we engineered stability and auto-regulation in the biological vanillin production system by applying the control theory and bacteria growth model in the design of the genetic circuit expressing the vanillin enzymes, Fcs and Ech.

The control theory can be applied in our genetic circuit through introducing bio-sensors such as the substrate sensor for ferulic acid and a time-delay element. The ferulic acid sensor is crucial for regulating the protein expression; it would only trigger the protein production when the substrate, ferulic acid is available. Further, in order for the cells to grow well, there must have a time delay before activating the bio-sensor. This is to ensure that in the presence of substrate inducers, cells growing from low cell density (e.g. single colony inoculation) would not experience overwhelming metabolic stress that may lead to growth retardation. The time-delay element would provide the cells some time to reach a higher cell density before activating the bio-sensor, so that the amount of substrate inducers per cell would be lower and thus less detrimental to growth.

Our mode of gene induction in bio-catalysts is more economically attractive. Compared to existing methods which use costly inducers such as IPTG, our method for vanillin production eliminates the need for external inducers and can bring considerable material cost savings in the industrial conversion of ferulic acid to vanillin. Our system auto-regulates the enzyme production based on the presence of ferulic acid as well as cell density.

Figure 5:
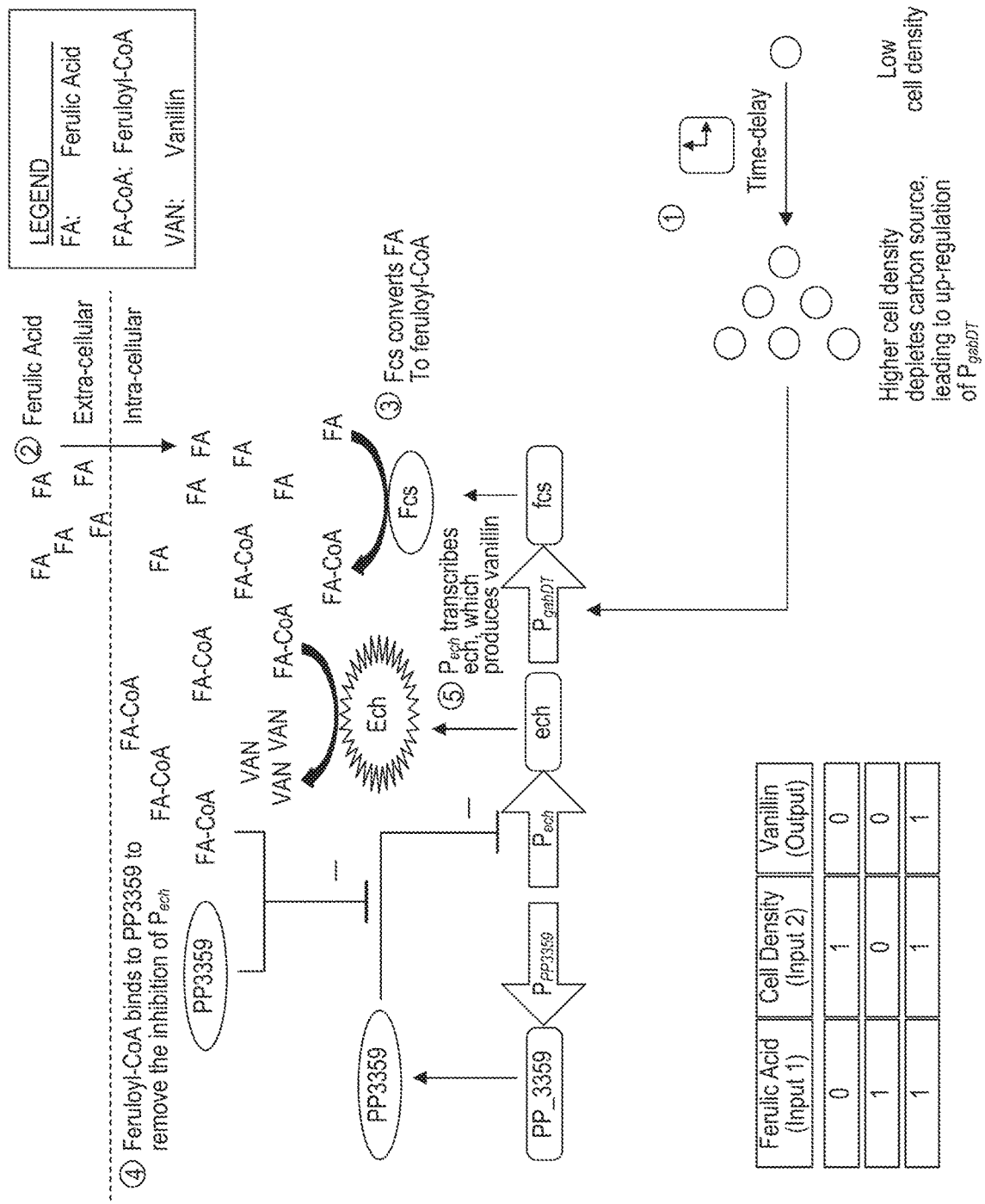
FIG. 5. A schematic overview of our genetic circuit. The genetic circuit is described in terms of the production of vanillin from ferulic acid implemented in *E. coli* BL21 (DE3)

An overview of the entire vanillin production system can be portrayed in FIG. 5. Implementation of $P_{gabDT}$ introduces the time-delay for the cells to reach a higher cell density such that the extra-cellular carbon source would be depleted due to increased utilization. Depletion of carbon source increases transcription of RpoS which activates $P_{gabDT}$ which transcribes fcs, thereby triggering the ferulic acid sensor. The ferulic acid sensor functions by detecting feruloyl-CoA, product of Fcs and activates the transcription of ech. Ech produced leads to conversion of feruloyl-CoA to vanillin.

Figure 6:
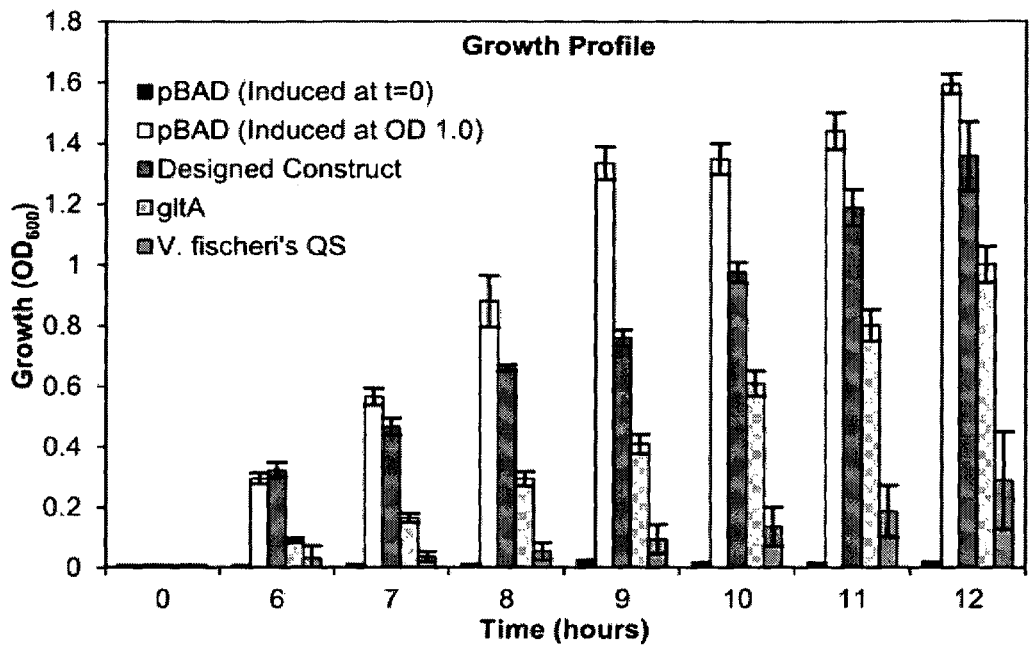
FIG. 6 The comparison of growth profiles of our designed construct ▌ in comparison with other constructs such as those that are artificially induced (pBAD) induced at t=0 ▌ and induced at $OD_{600}$ 1.0 ☐ as well as constructs designed using the quorum sensing lux regulon systems gltA ▦ and *Vibrio fischeri* ▦.

Our engineered E. coli is more stable and robust. In industrial bio-conversion, the size of bio-catalytic population is an important factor. We have created a genetic circuit that has minimal impact on cell growth. Implementation of a ferulic acid sensor helps in saving precious cellular metabolic resources, which in turn aids in the growth rate. Together with a time-delay element, the ferulic acid sensor is not activated until the cells reach a considerable density. This is so that the cells would not experience an overwhelming metabolic stress during early phase of growth where the substrate inducer per cell is high. Having a robust growth rate allows a quicker vanillin production. Our engineered E. co/i certainly has good growth profile over other types of genetic constructs (FIG. 6).

Figure 7:
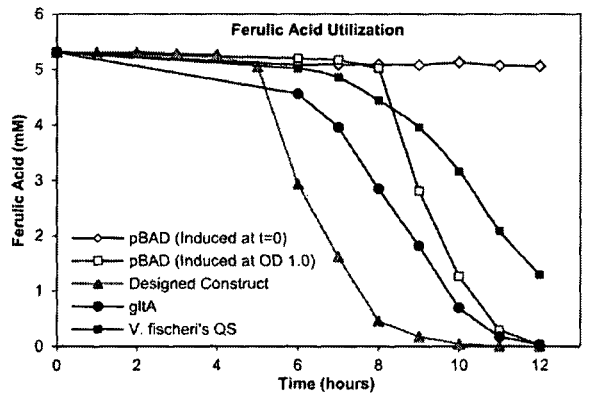
FIG. 7. The comparison of ferulic acid uptake rate and time to saturation of for vanillin production between our designed construct and other constructs. Our designed construct ▲ has the fastest ferulic acid uptake rate and the shortest time to saturation for vanillin production in comparison to pBAD induced at t=0 ◇; pBAD induced at $OD_{600}$ 1.0 ☐; gltA •; and *Vibrio fischeri* system ■.
Figure 7:
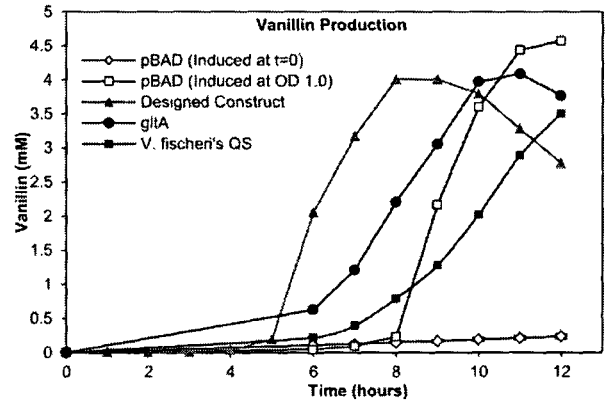

Our engineered E. coli has the fastest ferulic acid uptake rate and vanillin production rate. Compared to other genetic constructs such as the arabinose inducible system (pBAD), our designed construct has the best performance in terms of ferulic acid uptake and vanillin production (FIG. 7). This can be attributed to robust growth of the bio-catalytic cells. Our engineered E. coli also offers the fastest turnover rate (grams per liters per hour) compared to previously reported methods (Table 2). Having a quick turnover allows more vanillin to be produced in a fed-batch reaction per day.

TABLE 2

Compared to previous works, our construct (highlighted) has the fastest turnover rate.

| Strain | Mode of Induction | Media | Ferulic Acid added (g/L) | Vanillin produced (g/L) | Molar Conversion Efficiency (%) | Time Taken (hr) | Turnover rate (g/L per hr) | Source or Reference |
|---|---|---|---|---|---|---|---|---|
| E. coli XL1-Blue (pSKechE/Hfcs) | Artificial | MM | 0.74 | 0.27 | 47.37 | >12 | N.A. | Overhage et al. (1999) |
| E. coli XL1-Blue (pSKEHechfcs) | Artificial | MM | 1 | 0.26 | 32.50 | >12 | N.A. | Plaggenborg et al. (2001) |
| E. coli strain DH5a (pDAHEF) | Artificial | LB | 1 | 0.58 | 72.50 | 18 | 0.03 | Yoon et al. (2005) |
| E. coli JM109 (pBB1) | Constitutive | M9 | 0.64 | 0.35 | 69.70 | >12 | N.A. | Barghini et al. (2007) |
| E. coli DH5a (pTAHEF-gltA) | Leaky (No IPTG) | 2yT | 2 | 1.60 | 100 | 36 | 0.04 | Lee et al. (2009) |
| E. coli BL21(DE3) (pBbE8k-ech/fcs) | Artificial | M9 | 1 | 0.68 | 84.91 | 12 | 0.06 | This study |
| E. coli BL21(DE3) (Design construct) | Auto | M9 | 1 | 0.61 | 75.47 | 8 | 0.08 | This study |
| E. coli BL21(DE3) (Design construct-gltA) | Auto | M9 | 1 | 0.62 | 77.36 | 11 | 0.06 | This study |

TABLE 2-continued

Compared to previous works, our construct (highlighted)
has the fastest turnover rate.

| Strain | Mode of Induction | Media | Ferulic Acid added (g/L) | Vanillin produced (g/L) | Molar Conversion Efficiency (%) | Time Taken (hr) | Turnover rate (g/L per hr) | Source or Reference |
|---|---|---|---|---|---|---|---|---|
| E. coli BL21(DE3) (V. fischeri's QS) | Auto | M9 | 1 | 0.53 | 66.04 | 12 | 0.04 | This study |

We envisioned that our invention is highly applicable in the industrial production of vanillin from agro-industrial wastes. Agro-industrial wastes such as food and wood waste may serve as a source of ferulic acid. Given that ferulic acid rich bio-energy crops such as switchgrass are gaining support in global green energy industries, we anticipated ferulic acid source to be more available when ferulic acid is released as a by-product during biomass pre-treatment. With the increase availability in ferulic acid in near future, bio-production of vanillin from ferulic acid seems highly probable. Further, our invention may also value add to the biomass conversion process since the existing ferulic acid is often neglected and remains in the bio-compost which is to be served as fertilizer.

In addition, our invention is highly applicable in the economic context of industrial microbial bio-catalysis. Not only is our system free of costly inducers, our engineered E. coli can treat the substrate, ferulic acid as a signal for triggering the enzyme expression. This mode of auto-induction lowers the overall material cost. Towards the aim of industrial applicability, we have also engineered our system for stability and growth. By improving the viability of the engineered cells, we can achieve a large bio-catalytic population in the shortest time, thereby leading to a quicker vanillin production.

By "comprising" it is meant including, but not limited to, whatever follows the word "comprising". Thus, use of the term "comprising" indicates that the listed elements are required or mandatory, but that other elements are optional and may or may not be present.

By "consisting of" is meant including, and limited to, whatever follows the phrase "consisting of". Thus, the phrase "consisting of" indicates that the listed elements are required or mandatory, and that no other elements may be present.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

By "about" in relation to a given numerical value, such as for temperature and period of time, it is meant to include numerical values within 10% of the specified value.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

REFERENCES 1. de O. Buanafina, M. M. (2009) Feruloylation in Grasses: Current and Future Perspectives, *Molecular Plant* 2, 861-872.
2. Wong, D., Chan, V., Batt, S., Sarath, G., and Liao, H. (2011) Engineering *Saccharomyces cerevisiae* to produce feruloyl esterase for the release of ferulic acid from switchgrass, *J. Ind. Microbiol. Biotechnol.* 38, 1961-1967.
3. McClendon, S., Shin, H.-D., and Chen, R. (2011) Novel bacterial ferulic acid esterase from *Cellvibrio japonicus* and its application in ferulic acid release and xylan hydrolysis, *Biotechnol. Lett.* 33, 47-54.
4. Dodd, D., Kocherginskaya, S. A., Spies, M. A., Beery, K. E., Abbas, C. A Mackie, R. I., and Cann, I. K. O. (2009) Biochemical Analysis of β-D-Xylosidase and a Bifunctional Xylanase-Ferulic Acid Esterase from a Xylanolytic Gene Cluster in *Prevotella ruminicola* 23, *J. Bacteriol.* 191, 3328-3338.
5. Qi, M., Wang, P., Selinger, L. B., Yanke, L. J., Forster, R. J., and McAllister, T. A. (2011) Isolation and characterization of a ferulic acid esterase (Fae1A) from the rumen fungus *Anaeromyces mucronatus*, *J. Appl. Microbiol.* 110, 1341-1350.
6. Bartolomé, B., Faulds, C. B., Kroon, P. A., Waldron, K., Gilbert, H. J., Hazlewood, G., and Williamson, G. (1997) An *Aspergillus niger* esterase (ferulic acid esterase III) and a recombinant *Pseudomonas fluorescens* subsp. *cellulosa* esterase (Xy1D) release a 5-5' ferulic dehydrodimer (diferulic acid) from barley and wheat cell walls, *Appl. Environ. Microbiol.* 63, 208-212.
7. Yan, J., Hu, Z., Pu, Y., Charles Brummer, E., and Ragauskas, A. J. (2010) Chemical compositions of four switchgrass populations, *Biomass Bioenergy* 34, 48-53.

8. Bhathena, J., Kulamarva, A., Urbanska, A. M., Martoni, C., and Prakash, S. (2007) Microencapsulated bacterial cells can be used to produce the enzyme feruloyl esterase: preparation and in-vitro analysis, *Applied Microbiology & Biotechnology* 75, 1023-1029.
9. Yoon, S.-H., Lee, E.-G., Das, A., Lee, S.-H., Li, C., Ryu, H.-K., Choi, M.-S., Seo, W.-T., and Kim, S.-W. (2007) Enhanced Vanillin Production from Recombinant *E. coli* Using NTG Mutagenesis and Adsorbent Resin, *Biotechnol. Prog.* 23, 1143-1148.
10. Gasson, M. J., Kitamura, Y., McLauchlan, W. R., Narbad, A., Parr, A. J., Parsons, E. L. H., Payne, J., Rhodes, M. J. C., and Walton, N. J. (1998) Metabolism of Ferulic Acid to Vanillin, *J. Biol. Chem.* 273, 4163-4170.
11. Di Gioia, D., Luziatelli, F., Negroni, A., Ficca, A. G., Fava, F., and Ruzzi, M. (2011) Metabolic engineering of *Pseudomonas fluorescens* for the production of vanillin from ferulic acid, *J. Biotechnol.*
12. Overhage, J., Priefert, H., Rabenhorst, J., and Steinbuchel, A. (1999) Biotransformation of eugenol to vanillin by a mutant of *Pseudomonas* sp. strain HR199 constructed by disruption of the vanillin dehydrogenase (vdh) gene, *Appl. Microbiol. Biotechnol.* 52, 820-828.
13. Achterholt, S., Priefert, H., and Steinbüchel, A. (2000) Identification of *Amycolatopsis* sp. strain HR167 genes, involved in the bioconversion of ferulic acid to vanillin, *Appl. Microbiol. Biotechnol.* 54, 799-807.
14. Plaggenborg, R., Overhage, J., Steinbúchel, A., and Priefert, H. (2003) Functional analyses of genes involved in the metabolism of ferulic acid in *Pseudomonas putida* KT2440, *Appl. Microbiol. Biotechnol.* 61, 528-535.
15. Peng, X., Misawa, N., and Harayama, S. (2003) Isolation and Characterization of Thermophilic Bacilli Degrading Cinnamic, 4-Coumaric, and Ferulic Acids, *Appl. Environ. Microbiol.* 69, 1417-1427.
16. Plaggenborg, R., Steinbuchel, A., and Priefert, H. (2001) The coenzyme A-dependent, non-β-oxidation pathway and not direct deacetylation is the major route for ferulic acid degradation in *Delftia acidovorans, FEMS Microbiol. Lett.* 205, 9-16.
17. Muheim, A., and Lerch, K. (1999) Towards a high-yield bioconversion of ferulic acid to vanillin, *Appl. Microbiol. Biotechnol.* 51, 456-461.
18. Yoon, S.-H., Li, C., Lee, Y.-M., Lee, S.-H., Kim, S.-H., Choi, M.-S., Seo, W.-T., Yang, J.-K., Kim, J.-Y., and Kim, S.-W. (2005) Production of vanillin from ferulic acid using recombinant strains of *Escherichia coli, Biotechnology and Bioprocess Engineering* 10, 378-384.
19. Lee, E.-G., Yoon, S.-H., Das, A., Lee, S.-H., Li, C., Kim, J.-Y., Choi, M.-S., Oh, D.-K., and Kim, S.-W. (2009) Directing vanillin production from ferulic acid by increased acetyl-CoA consumption in recombinant *Escherichia coli, Biotechnol. Bioeng.* 102, 200-208.
20. Barghini, P., Di Gioia, D., Fava, F., and Ruzzi, M. (2007) Vanillin production using metabolically engineered *Escherichia coli* under non-growing conditions, *Microbial Cell Factories* 6, 13.
21. Yamada, M., Okada, Y., Yoshida, T., and Nagasawa, T. (2008) Vanillin production using *Escherichia* cells overexpressing isoeugenol monooxygenase of *Pseudomonas putida, Biotechnol. Lett.* 30, 665-670.
22. Nocadello, S., and Swennen, E. (2012) The new pLAI (lux regulon based auto-inducible) expression system for recombinant protein production in *Escherichia coli, Microbial Cell Factories* 11, 3.
23. Zhang, F., Carothers, J. M., and Keasling, J. D. (2012) Design of a dynamic sensor-regulator system for production of chemicals and fuels derived from fatty acids, *Nat Biotech advance online publication*.
24. Saeidi, N., Wong, C. K., Lo, T.-M., Nguyen, H. X., Ling, H., Leong, S. S. J., Poh, C. L., and Chang, M. W. (2011) Engineering microbes to sense and eradicate *Pseudomonas aeruginosa*, a human pathogen, *Mol Syst Biol* 7.

The invention claimed is:

1. A bacterial recombinant expression system comprising:
   (i) a first gene encoding for a first enzyme linked to a first promoter, wherein the first enzyme is a feruloyl CoA synthetase; wherein the first promoter is activatable by a RpoS transcription factor and selected from a gabDT promoter; an otsA promoter; a katE promoter; an osmY promoter; a yhiUV promoter; an ecnB promoter; a dps promoter; an osmE promoter; a rpsV promoter, and a tnaA promoter; and wherein the first gene linked to the first promoter is a different gene than a gene naturally linked to the first promoter;
   (ii) a second gene encoding for a second enzyme capable of using the product generated by the first enzyme as a substrate, wherein the second gene is operably linked to a second promoter, wherein the second promoter is inducible by the product generated by the first enzyme;
   (iii) optionally, a third gene encoding a transcription factor that represses expression of the second gene in the absence of the product generated by the first enzyme, wherein the third gene is operably linked to a third promoter that regulates expression of the third gene.

2. The recombinant expression system of claim 1, wherein the recombinant expression system is a heterologous expression system.

3. The recombinant expression system of claim 1, wherein the first promoter sequence comprises a consensus sequence set forth in SEQ ID NO: 1.

4. The recombinant expression system of claim 3, wherein the first promoter comprises a gabDT promoter.

5. The recombinant expression system of claim 4, wherein the first promoter has the nucleotide sequence set forth in SEQ ID NO:3.

6. The recombinant expression system of claim 1, wherein the first promoter is activatable by the RpoS transcription factor comprising the amino acid sequence set forth in SEQ ID NO:2.

7. The recombinant expression system of claim 1, wherein the substrate of the enzyme encoded by the first gene is a hydroxycinnamic acid or derivative thereof selected from the group consisting of ferulic acid, caffeic acid, and p-coumaric acid.

8. The recombinant expression system of claim 1, wherein the first gene has the nucleotide sequence set forth in SEQ ID NO:4.

9. The recombinant expression system 1 of claim 1, wherein the second promoter has the nucleotide sequence set forth in SEQ ID NO:6.

10. The recombinant expression system of claim 1, wherein the second gene has the nucleotide sequence set forth in SEQ ID NO:5.

11. A recombinant nucleic acid molecule comprising:
   a. a first gene encoding for a first enzyme linked to a first promoter, wherein the first enzyme is a feruloyl CoA synthetase; wherein the first promoter is activatable by a RpoS transcription factor and selected from a gabDT promoter; an otsA promoter; a katE promoter; an osmY promoter; a yhiUV promoter; an ecnB promoter; a dps promoter; an osmE promoter; a rpsV promoter, and a tnaA promoter; and wherein the first gene linked to the first promoter is a different gene than a gene naturally linked to the first promoter;
   b. a second gene encoding for a second enzyme capable of using the product generated by the first enzyme as a substrate, wherein the second gene is operably linked to a second promoter, wherein the second promoter is inducible by the product generated by the first enzyme;
   c. optionally, a third gene encoding a transcription factor that represses expression of the second gene in the absence of the product generated by the first enzyme, wherein the third gene is operably linked to a third promoter that regulates expression of the third gene.

12. The recombinant nucleic acid molecule of claim 11, wherein the recombinant nucleic acid molecule is comprised in a plasmid.

13. The recombinant nucleic acid molecule of claim 12, wherein the plasmid is heterologous.

14. The recombinant nucleic acid molecule of claim 11, wherein the first promoter sequence comprises a consensus sequence set forth in SEQ ID NO: 1.

15. The recombinant nucleic acid molecule of claim 14, wherein the first promoter comprises a gabDT promoter.

16. The recombinant nucleic acid molecule of claim 15, wherein the first promoter has the nucleotide sequence set forth in SEQ ID NO:3.

17. The recombinant nucleic acid molecule of claim 11, wherein the first promoter is activatable by the RpoS transcription factor comprising amino acid sequence set forth in SEQ ID NO:2.

18. The recombinant nucleic acid molecule of claim 11, wherein the substrate of the enzyme encoded by the first gene is a hydroxycinnamic acid or derivative thereof selected from the group consisting of ferulic acid, caffeic acid, and p-coumaric acid.

19. The recombinant nucleic acid molecule of claim 11, wherein the first gene has the nucleotide sequence set forth in SEQ ID NO:4.

20. The recombinant nucleic acid molecule of claim 11, wherein the second promoter has the nucleotide sequence set forth in SEQ ID NO:6.

21. The recombinant nucleic acid molecule of claim 11, wherein the second gene has the nucleotide sequence set forth in SEQ ID NO:5.

22. A method of converting a substrate to a product comprising the steps of:
   a. expressing the first and second enzymes using the recombinant expression system of claim 1; and
   b. isolating the product generated from the second enzyme.

23. The method of claim 22, wherein the product is a hydroxybenzaldehyde.

24. The method of claim 22, wherein the product is vanillin.

25. The method of claim 22, wherein the product is p-hydroxybenzoate.

* * * * *

SEQUENCE LISTING

```
<160> NUMBER OF SEQ ID NOS: 8

<210> SEQ ID NO 1
<211> LENGTH: 14
<212> TYPE: DNA
<213> ORGANISM: Artificial Sequence
<220> FEATURE:
<223> OTHER INFORMATION: time delay promotor consensus sequence
      activatable by RpoS sigma factor
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (5)..(7)
<223> OTHER INFORMATION: n is a, c, g, or t
<220> FEATURE:
<221> NAME/KEY: misc_feature
<222> LOCATION: (9)..(14)
<223> OTHER INFORMATION: n is a, c, g, or t

<400> SEQUENCE: 1
nctannntnn nnnn                                                    14

<210> SEQ ID NO 2
<211> LENGTH: 330
<212> TYPE: PRT
<213> ORGANISM: Escherichia coli
```

<400> SEQUENCE: 2

```
Met Ser Gln Asn Thr Leu Lys Val His Asp Leu Asn Glu Asp Ala Glu
1               5                   10                  15

Phe Asp Glu Asn Gly Val Glu Val Phe Asp Glu Lys Ala Leu Val Glu
            20                  25                  30

Gln Glu Pro Ser Asp Asn Asp Leu Ala Glu Glu Leu Leu Ser Gln
        35                  40                  45

Gly Ala Thr Gln Arg Val Leu Asp Ala Thr Gln Leu Tyr Leu Gly Glu
50                  55                  60

Ile Gly Tyr Ser Pro Leu Leu Thr Ala Glu Glu Val Tyr Phe Ala
65                  70                  75                  80

Arg Arg Ala Leu Arg Gly Asp Val Ala Ser Arg Arg Met Ile Glu
                85                  90                  95

Ser Asn Leu Arg Leu Val Val Lys Ile Ala Arg Arg Tyr Gly Asn Arg
            100                 105                 110

Gly Leu Ala Leu Leu Asp Leu Ile Glu Glu Gly Asn Leu Gly Leu Ile
            115                 120                 125

Arg Ala Val Glu Lys Phe Asp Pro Glu Arg Gly Phe Arg Phe Ser Thr
130                 135                 140

Tyr Ala Thr Trp Trp Ile Arg Gln Thr Ile Glu Arg Ala Ile Met Asn
145                 150                 155                 160

Gln Thr Arg Thr Ile Arg Leu Pro Ile His Ile Val Lys Glu Leu Asn
                165                 170                 175

Val Tyr Leu Arg Thr Ala Arg Glu Leu Ser His Lys Leu Asp His Glu
            180                 185                 190

Pro Ser Ala Glu Glu Ile Ala Glu Gln Leu Asp Lys Pro Val Asp Asp
        195                 200                 205

Val Ser Arg Met Leu Arg Leu Asn Glu Arg Ile Thr Ser Val Asp Thr
210                 215                 220

Pro Leu Gly Gly Asp Ser Glu Lys Ala Leu Leu Asp Ile Leu Ala Asp
225                 230                 235                 240

Glu Lys Glu Asn Gly Pro Glu Asp Thr Thr Gln Asp Asp Met Lys
                245                 250                 255

Gln Ser Ile Val Lys Trp Leu Phe Glu Leu Asn Ala Lys Gln Arg Glu
            260                 265                 270

Val Leu Ala Arg Arg Phe Gly Leu Leu Gly Tyr Glu Ala Ala Thr Leu
            275                 280                 285

Glu Asp Val Gly Arg Glu Ile Gly Leu Thr Arg Glu Arg Val Arg Gln
        290                 295                 300

Ile Gln Val Glu Gly Leu Arg Arg Leu Arg Glu Ile Leu Gln Thr Gln
305                 310                 315                 320

Gly Leu Asn Ile Glu Ala Leu Phe Arg Glu
                325                 330
```

<210> SEQ ID NO 3
<211> LENGTH: 59
<212> TYPE: DNA
<213> ORGANISM: Escherichia coli

<400> SEQUENCE: 3
ggcagcgaca tcagcaattc ctattggtgc gcatattgta gcaaggtaca aacgctgtt       59

<210> SEQ ID NO 4
<211> LENGTH: 1884

```
<212> TYPE: DNA
<213> ORGANISM: Pseudomonas putida

<400> SEQUENCE: 4
atgaataacg aagcccgctc agggtcgacc gaccctggcc aacgtccgcg ctaccgccag      60
gtggccatcg gcatcccca ggtgcaggtc agtcacgtcg acgacgtgct gcgcatgcaa     120
cctgtcgagc cactggcgcc gctgccggcg cgcctgctcg agcgcctggt gcattgggcc     180
caggtgcgcc cggacaccac tttcatcgcg gcacgccagg cagacggtgc ctggcgttcg     240
atcagctacg tgcagatgct cgccgatgtg cgcaccatcg ccgccaactt gctaggactg     300
ggcctcagtg ccgagcgccc gctggcgctg ctttccggca cgacatcga acacctgcaa      360 atcgccctcg gcgccatgta tgccggtatt gcctattgcc cggtgtcgcc ggcctacgcg     420
ctgttgtcgc aagacttcgc caagttgcgc catgtctgcg aggtgctcac ccccggagtg     480
gtcttcgtca gcgacagcca gccgttccag cgcgccttcg aggcggtgct ggacgattcg     540
gtcggcgtga tcagcgtgcg tggccaggtc gcaggtcgcc cccatataag cttcgacagc     600
ctgttgcaac cgggtgacct ggcggcggcc gatgcggctt cgccgccac cgggccggac     660 accatcgcca aattcctctt cacctcgggc tcgaccaagc tgcccaaggc ggtgatcacc     720
acccagcgca tgctgtgcgc caatcagcag atgcttctgc agactttttcc gacgttcgcc     780 gaggagccgc cggtgctggt ggactggctg ccgtggaacc acacgttcgg cggtagccac     840
aacctcggca tcgtgcttta caacgggggc agtttctacc tggacgccgg caagccgacc     900
ccgcaaggct tcgccgagac cttgcgcaat ttgcgcgaga tttcccccac ggcctacctc     960
accgtaccca agggctggga ggaactggtc aaggcactgg agcaggaccc cgcgctacgc    1020
gaggtgttct tgcccgcat caagctgttc ttctttgccg ccgcaggcct gtcgcaaagc    1080
gtctgggacc ggctggaccg cattgccgag caacactgtg gcgaacgcat ccgcatgatg    1140
gccggccttg gcatgaccga agcctcgcca tcgtgcacct tcaccaccgg gcctttgtcg    1200
atggccggct atgtcgggct gccggcacct ggctgcgaag tgaagctggt gccggtgggc    1260
gacaagctcg aggcgcgctt ccgtggcccc catatcatgc cgggctactg gcgctcgccg    1320
cagcagaccg ccgaggcgtt cgacgaggag ggcttctact gttcgggcga cgcgttgaag    1380
ctggccgatg ccaggcagcc cgagcttggc ctgatgttcg atggccgtat cgctgaggac    1440
ttcaaacttt cgtccggggt attcgtcagt gtcgggccgc tgcgcaaccg cgcagtgctg    1500
gagggctcgc cttacgtaca ggacatcgtg gtcaccgcgc cggaccgtga atgcctgggc    1560
ctgctggtgt tcccgcgtct gcccgagtgt cggcgcctgg ccgggctggc agaggatgcc    1620
agcgatgcgc gggtgctggc caacgacacc gtgcgcagtt ggttcgctga ctggctggag    1680
cgcttgaacc gcgatgccca aggcaacgcc agccgtatcg aatggctgtc gctgctggcc    1740
gagccgccgt cgatcgacgc cggtgaaatc accgacaagg gctcgatcaa tcagcgcgcc    1800
gtgctgcagc ggcgcgccgc tcaggtcgag gcgctgtacc gtggcgaaga ccccgacgca    1860
ttgcacgcca aggtgcggcc ttaa                                          1884

<210> SEQ ID NO 5
<211> LENGTH: 831
<212> TYPE: DNA
<213> ORGANISM: Pseudomonas putida

<400> SEQUENCE: 5
atgagcaaat acgaaggccg ctggaccacc gtgaaggtcg aactggaagc gggcatcgcc      60
```

```
tgggtgaccc tcaatcgccc ggaaaaacgc aatgccatga gccccaccct gaaccgggaa    120
atggtcgacg tgctggaaac ccttgagcag gacgctgacg ctggcgtgct ggtattgacc    180
ggtgccggcg agtcctggac cgccggcatg gacctgaagg agtacttccg cgaggtggac    240
gccggcccgg aaatcctcca ggaaaagatt cgtcgcgaag cctcgcaatg caatggaag     300 ttgctgcgtc tgtatgccaa accgaccatc gccatggtca acggctggtg cttcggcggc    360
ggcttcagcc cactggtggc atgcgacctg gcgatctgcg ccaacgaagc gaccttcggc    420
ctgtcggaaa tcaactgggg catcccgcct ggtaacctgg tcagcaaggc catggccgat    480
accgttggcc atcgtcagtc gctgtactac atcatgaccg gcaagacctt cgatggtcgc    540
aaggctgccg agatgggcct ggtgaacgac agtgtgccgc tggccgagct gcgtgaaacc    600
acccgcgagt ggcgctgaa cctgctggaa aagaacccgg tggtgctgcg tgccgcgaag    660
aatggcttca gcgttgccg cgagctgacc tgggaacaga acgaggacta cctctacgcc    720
aagctcgacc agtcgcgcct gctggacact accggcggcc gcgagcaggg catgaagcag    780
ttcctcgacg acaagagcat caagccaggc ctgcaggcct acaagcgctg a             831

<210> SEQ ID NO 6
<211> LENGTH: 183
<212> TYPE: DNA
<213> ORGANISM: Pseudomonas putida

<400> SEQUENCE: 6
caggtttcat gctcctcgat catgggtaat aaagttacct attttgcctg tccttatgcg    60
attcggctag agaggttctg gaaaaaggca gcgcgcctaa ccccaggaca agataaaat    120 tgttaatggt taattgacat aactaatttg acccgttagc gtggccccat cacctcgaac    180
aac                                                                  183

<210> SEQ ID NO 7
<211> LENGTH: 471
<212> TYPE: DNA
<213> ORGANISM: Pseudomonas putida

<400> SEQUENCE: 7
atggctaggt ctgcccgtag taccgacgac gcttgcgtgg ctgctcctgt gggagaaggg    60
gtgcttgaag acttgatcgg ctacgccttg cgacgcgcgc aattgaagct gtttcagaac    120
cttattgccc ggctctcggc ccatgacctg cgcccggccc aattttccgc cctggcgatc    180
atcgaccaga accccgggct gatgcaggcc gacctggcgc gtgcgttggc aatcgacccc    240
ccgcaagtcg tgccaatgct gaacaaactg aagagcgcg cgctggccgt gcgcgtgcgg    300
tgcaaaccgg acaagcgctc gtatgggatt ttcctgagca atcgggcga ggccctgttg    360 aaggagttga agcacatcgc cgccgacagc gatcaccagg cgacatccaa cctctcggat    420
gacgaaagga ctgaactgtt gaggttattg aagaaaatct accgggactg a             471

<210> SEQ ID NO 8
<211> LENGTH: 156
<212> TYPE: PRT
<213> ORGANISM: Pseudomonas putida

<400> SEQUENCE: 8

Met Ala Arg Ser Ala Arg Ser Thr Asp Asp Ala Cys Val Ala Ala Pro
1               5                   10                  15

Val Gly Glu Gly Val Leu Glu Asp Leu Ile Gly Tyr Ala Leu Arg Arg
            20                  25                  30
```

```
Ala Gln Leu Lys Leu Phe Gln Asn Leu Ile Ala Arg Leu Ser Ala His
        35                  40                  45

Asp Leu Arg Pro Ala Gln Phe Ser Ala Leu Ala Ile Ile Asp Gln Asn
    50                  55                  60

Pro Gly Leu Met Gln Ala Asp Leu Ala Arg Ala Leu Ala Ile Asp Pro
65                  70                  75                  80

Pro Gln Val Val Pro Met Leu Asn Lys Leu Glu Glu Arg Ala Leu Ala
                85                  90                  95

Val Arg Val Arg Cys Lys Pro Asp Lys Arg Ser Tyr Gly Ile Phe Leu
                100                 105                 110

Ser Lys Ser Gly Glu Ala Leu Leu Lys Glu Leu Lys His Ile Ala Ala
        115                 120                 125

Asp Ser Asp His Gln Ala Thr Ser Asn Leu Ser Asp Asp Glu Arg Thr
    130                 135                 140

Glu Leu Leu Arg Leu Leu Lys Lys Ile Tyr Arg Asp
145                 150                 155
```